(12) United States Patent
Phipps

(10) Patent No.: US 6,579,231 B1
(45) Date of Patent: Jun. 17, 2003

(54) PERSONAL MEDICAL MONITORING UNIT AND SYSTEM

(75) Inventor: Eric T. Phipps, Colorado Springs, CO (US)

(73) Assignee: MCI Communications Corporation, Washington, DC (US)

( * ) Notice: Subject to any disclaimer, the term of this patent is extended or adjusted under 35 U.S.C. 154(b) by 0 days.

(21) Appl. No.: 09/049,542

(22) Filed: Mar. 27, 1998

(51) Int. Cl.[7] .......... A61B 5/00; G08B 23/00; H04M 11/00
(52) U.S. Cl. .......... 600/300; 600/301; 128/903; 128/920; 340/573.1; 604/65; 455/404
(58) Field of Search .......... 600/300, 301, 600/322, 595, 587, 316, 310; 128/900, 903–905, 920–925; 340/573.1–573.7; 607/32, 60; 342/457; 705/2–4; 455/404; 604/65

(56) References Cited

U.S. PATENT DOCUMENTS

| | | | |
|---|---|---|---|
| 4,129,125 A | * | 12/1978 | Lester et al. .......... 600/300 |
| 5,204,670 A | * | 4/1993 | Stinton .......... 340/573.1 |
| 5,319,355 A | * | 6/1994 | Russek .......... 340/573 |
| 5,544,661 A | * | 8/1996 | Davis et al. .......... 600/300 |
| 5,652,570 A | * | 7/1997 | Lepkofker .......... 600/300 |
| 5,658,250 A | * | 8/1997 | Blomquist et al. .......... 600/300 |
| 5,722,418 A | * | 3/1998 | Bro .......... 600/509 |
| 5,772,586 A | * | 6/1998 | Heinonen et al. .......... 600/300 |
| 5,872,505 A | * | 2/1999 | Wick et al. .......... 128/904 |
| 5,902,234 A | * | 5/1999 | Webb .......... 600/300 |
| 5,929,782 A | * | 7/1999 | Stark et al. .......... 128/903 |
| 5,931,791 A | * | 8/1999 | Saltzstein et al. .......... 600/513 |
| 5,959,529 A | * | 9/1999 | Kail, IV | |
| 5,961,451 A | * | 10/1999 | Reber et al. .......... 600/322 |
| 6,024,699 A | * | 2/2000 | Surwit et al. .......... 600/300 |
| 6,198,394 B1 | * | 3/2001 | Jacobsen et al. .......... 340/573.1 |
| 6,292,698 B1 | * | 9/2001 | Duffin et al. .......... 607/32 |

* cited by examiner

Primary Examiner—Max F. Hindenburg
Assistant Examiner—Michael Astorino

(57) ABSTRACT

A portable unit worn by a subject, comprising a medical monitoring device, a data processing module with memory and transmitter for collecting, monitoring, and storing the subject's physiological data and also issuing the subject's medical alarm conditions via wireless communications network to the appropriate location for expeditious dispatch of assistance. The unit also works in conjunction with a central reporting system for long term collection and storage of the subject's physiological data. The unit may have the capability to automatically dispense chemicals that may alleviate or assist in recovery from an illness.

36 Claims, 3 Drawing Sheets

PERSONAL MEDICAL MONITORING UNIT AND SYSTEM

BACKGROUND OF THE INVENTION

1. Field of the Invention

The present invention relates generally to a medical monitoring unit or device for the continued examination and care of a subject. More particularly, the present invention is directed to a medical monitoring device and system for the continuous storing of a subject's current physiological or medical data, the evaluation of said data enabling the early detection of adverse health conditions should they arise, and the providing of real time notification of such health conditions to the appropriate person or persons such that a proper and expeditious response may be taken.

2. Prior Art

The benefits of being able to monitor and/or study various medical characteristics of a subject on a continuous basis, store and evaluate the data of those chosen aspects of the subject and initiate a particular response based on said evaluation are numerous. To accomplish such a feat in today's world would encompass a huge undertaking.

The most obvious use of the present invention would be in connection with individuals suffering from specific health problems. Any individual with a continuing illness such as heart disease or asthma, ideally needs to be monitored continually for the slightest recurring signs of those health problems. Although the medical industry has many tools for monitoring an individual's activities and evaluating their personal responses to those activities, a person must traditionally travel periodically to a medical facility in order to obtain the proper medical care and diagnosis. Once at the facility, the individual is often hooked up to some type of a monitoring instrument and is thereafter usually confined to the particular area for the duration of the session. In some cases, this may be several hours or more. While the monitoring equipment is attached to the individual, movement by the individual is either severely restricted or not permitted at all.

Moreover, the results of these existing procedures and tests, when they are finally reviewed and interpreted by the doctor or medical technician, only give a glimpse of the subject's activity and physiological data at the time of the monitoring. Today's monitoring equipment does not provide the physician or health care providers with nearly enough information on the subject's general conditions prior to or after the tests are performed. That is, in order to be able to establish a more accurate medical diagnosis, doctors would greatly benefit from observing the history of a subject's medical data for a longer duration than the time permitted in the medical facilities. For various obvious reasons, such as the time needed to perform these tests, the costs of the tests and the headaches of trying to schedule the required number of visits which would enable a full evaluation of a subject's health history, such an observation of an individual would be infeasible.

Another major problem for many individuals is getting prompt medical attention as soon as a medical problem occurs. The providing of expeditious medical care is sometimes crucial to the individual's ability to recover. For example, a heart attack victim has a significantly greater chance of full recovery if medical attention is received within the first few hours after signs of a heart attack are detected or the actual heart attack has occurred. Unfortunately, most of the time, an individual does not recognize the symptoms which would indicate that they were at risk. Often, by the time the individual does realize that help is needed, they are incapable of calling for emergency assistance. Yet another problem is providing the emergency medical services attending the individual with quick and accurate information which would lead to a successful diagnosis and treatment of the problem.

Portable EKG monitoring devices are known which collect medical data on cardiac functions from a plurality of sensors. After a predefined period, normally twenty-four hours, the data is transferred to a computer or strip recorder for analysis by skilled medical personnel in a conventional manner. Although such a device is very useful, there is still a time delay before the collected data is reviewed and analyzed.

Accordingly, there is still a need for a service that can provide for the continuous collection, monitoring and storing a subject's physiological data while allowing the subject complete freedom and mobility.

SUMMARY OF THE INVENTION

The present invention is directed to the continuous real time collection, monitoring and storage of an individual's physiological data without interrupting or incapacitating any aspect of the individual's everday life. In addition, the monitoring device and system of the present invention can send out a distress call when the individual's vital signs reach a dangerous level or stop altogether.

The present invention uses a standard microcomputer in connection with various types of medical monitoring devices, and utilizes wireless communications technology known in the art. More particularly, the monitoring device employs software having the capability to monitor a subject's vital signs, record, collect and store the data. The stored information may then be downloaded into a computer to be analyzed. The computer may be located anywhere, including in a hospital, a clinic, the individuals home, or a physician's office. In addition, the monitoring device may also be able to provide real time information to the monitored subject at a touch of a button.

If the monitoring device detects abnormal behavior or stressful conditions in the subject being monitored, it can alert and notify the subject or the appropriate people such that the subject's current activities can be limited accordingly to combat the detected adverse conditions. When, and if, a subject's vital signs stop or reach a dangerous level, the monitoring device may emit some type of alarm, such as a loud beeping sound, to attract the attention of the subject and/or anyone in the immediate vicinity of the subject. If the subject is unable to respond to the alarm condition, the device may send out a distress call. The device may be programmed such that a call to 911 is immediately made and the subject's name and medical history are provided therewith. At the same time, the present device may also provide the 911 operator with the subject's exact location, by sending them a global positioning satellite (GPS) coordinate stored in the device.

Accordingly, it is an object of the present invention to provide a personal medical monitoring unit which may be worn on a subject and carried anywhere. The unit may be equipped to store current medical data and detect any pre-defined alarm conditions, such as heart failure. Upon an occurrence of one or more of such alarm conditions, the unit provides a central reporting system with emergency information for the efficient dispatching of emergency assistance.

It is another object of the present invention to combine the advantages of long-range navigation systems such as a global positioning system (GPS) for locating the subject at the time of the health crisis. The extensive communications capabilities of a cellular telephone or a two way pager would provide the most expeditious emergency assistance.

It is another object of the present invention to provide some type of notification feature, such as a beeper and/or vibrating mechanism, to inform the subject, or people nearby, of a detected condition.

It is still another object of the present invention to provide a service for continuous real time collection and long term storage of a remote subject's medical data via wireless communications technology.

BRIEF DESCRIPTION OF THE DRAWINGS

Preferred embodiments of the present invention will now be described, by way of example only, with reference to the accompanying drawings, in which.

DETAILED DESCRIPTION OF PREFERRED EMBODIMENTS

Figure 1:
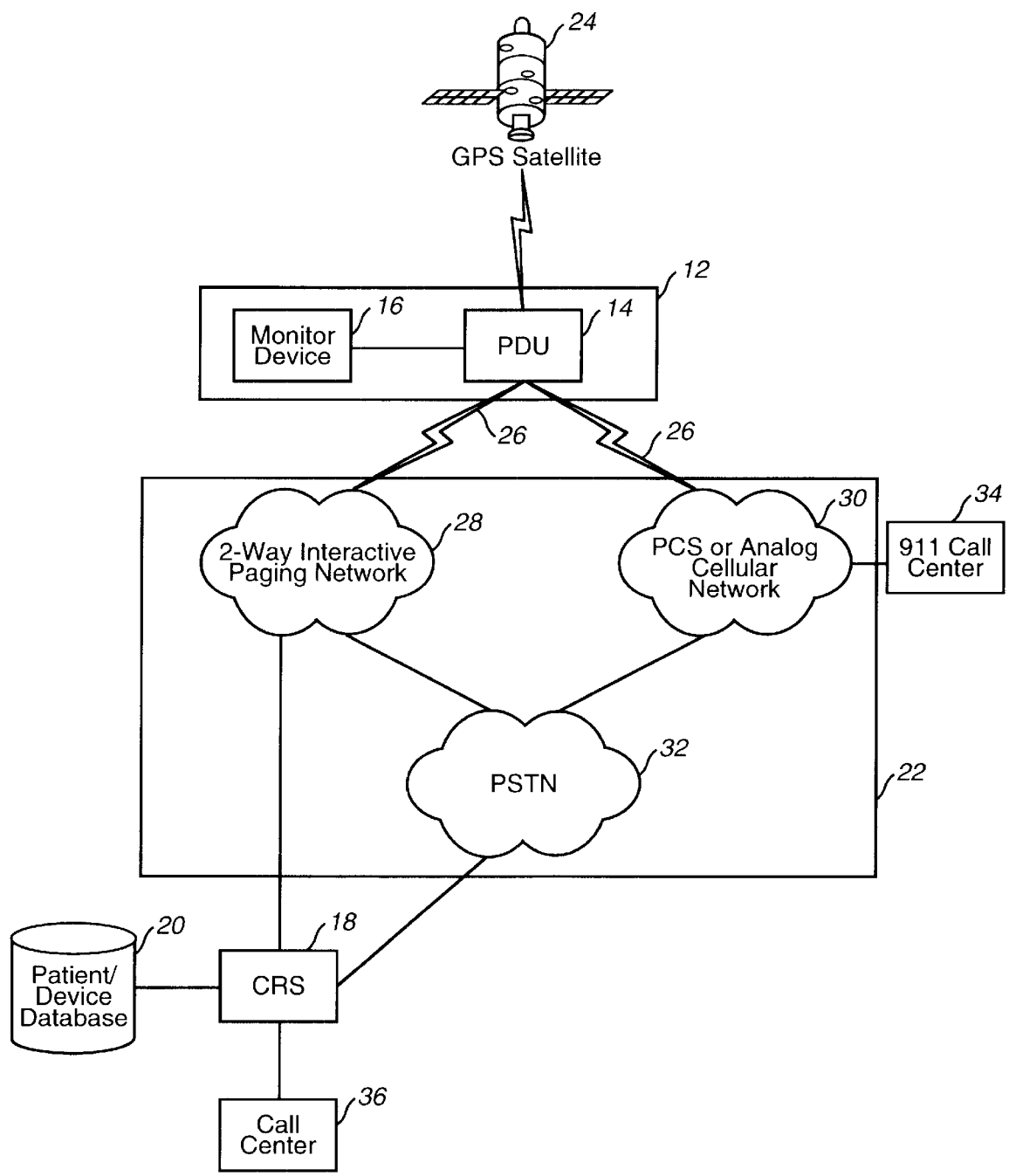
FIG. 1 is a block diagram illustrating the present invention in a preferred embodiment.

FIG. 1 is a block diagram illustrating the present invention in its preferred embodiment. That is, FIG. 1 illustrates the present invention as a personal medical monitoring unit and system. The unit 12 is typically comprised of a personal data unit(PDU) 14 and a monitoring device 16. It should be noted that the PDU 14 and the monitoring device 16 do not need to be in separate housings as illustrated in FIG. 1, but may be confined in a single unit as indicated at 12. The system is generally comprised of the PDU 14 and the monitoring device 16, in conjunction with a Central Reporting System (CRS) 18, a Subject/Device Database 20, and a communications network 22 as shown.

The monitoring device 16 is usually worn by a user, i.e. the subject to be monitored—typically a "patient". Of course, the monitored subject is not limited to "patients" per se, but can be used with respect to anybody. That is, people with no past medical history can use the present monitoring device simply as a safeguard against any health risks that may arise; athletes may employ the present devices to monitor their own physical condition during competition, practice or training; parents may use the present invention to monitor and care for their children or infants; contained facilities, such as prisons, can monitor their inhabitants (such as the guards and prisoners); the present device can even be used to monitor the physical characteristics of an animal or pet. The possibilities are endless.

The monitoring device of the present invention can be any type of medical monitoring device, including those which monitor heart rate or pulse, breathing rate, blood pressure, heart EKG activity, or body temperature. The PDU 14 includes a transmitter, memory, and a processor. The transmitter may be an interactive pager, a Personal Communications Services (PCS) network digital or analog cellular phone.

The PDU 14 may also include a long-range navigation system receiver such as a global positioning system (GPS) receiver; data ports for uploading and downloading information such as medical information, addresses, and thresholds; and a number of input/output devices such as an LCD display monitor, push buttons, a beeper, and a vibration mechanism.

In a preferred embodiment, the PDU 14 continuously monitors a subject's medical data values as it receives them from the medical monitoring device 16 and stores them in its memory. In addition, the PDU 14 constantly receives communications signals from the well-known GPS satellites 24, which is a group of three geostationary satellites used for determining one's geographical location. GPS coordinates are also stored in memory in the PDU 14. When the monitoring device 16 detects a certain condition (e.g., loss of pulse), it triggers the PDU 14 to take action in accordance with pre-determined instructions stored in PDU memory. An exemplary action is to issue an emergency page or call via a wireless communications network 26.

Two embodiments of communications networks are shown in FIG. 1. In one example, a two-way interactive paging network 28 is used, and the PDU's transmitter is an interactive paging device. The PDU issues an automatic page which includes an alphanumeric string retrieved from PDU memory. The page is sent over a paging network 28 to a Central Reporting System (CRS) 18. Alternatively, the page may be sent over a Public Switched Telephone Network (PSTN) 32 to the CRS 18.

In a second example of communications networks, a Personal Communications Services (PCS) 30, which is a digital cellular network, or an analog cellular network is used. The PDU's transmitter is a PCS phone, for example. The PDU 14, when triggered by the user or the monitoring device 16, issues a PCS phone call. A dialing sequence is stored in PDU memory. The PDU PCS phone seizes a channel, sets up a call on the PCS network, and completes a call. A call may be completed to a 911 Call Center 34, or to the CRS 18. Calls may be completed over the PCS cellular network 30, or via the PSTN 32.

The CRS 18 is a server computer that receives emergency calls or pages from a plurality of PDUs 14, and takes action in accordance with records and instructions previously entered in a Subject/Device Database 20. Typically, the CRS 18 will notify a Call Center 36 of an emergency situation. When the CRS 18 receives the emergency call or page from the PDU 14, it references the Subject/Device Database 20 to identify the device and subject, based on a device identifier that is included in the emergency page/call. Each device and/or subject has a record in the Subject/Device Database 20. The record includes subject information. (e.g., name, address, medical conditions, etc.) and medical instructions for responding to an emergency page or call. The CRS 18 may issue a call to an agent at a Call Center 36. This call may be text-based, so that the CRS 18 can send a text message to the Call Center 36 agent to indicate that a certain PDU for a certain subject has detected a certain condition, and that medical attention may be needed.

The emergency page or call may also contain the subject's current GPS coordinates. The CRS 18 translates these coordinates to a recognizable geographical reference, and provides the subject's accurate location in the call information provided to the Call Center 36.

Figure 2:
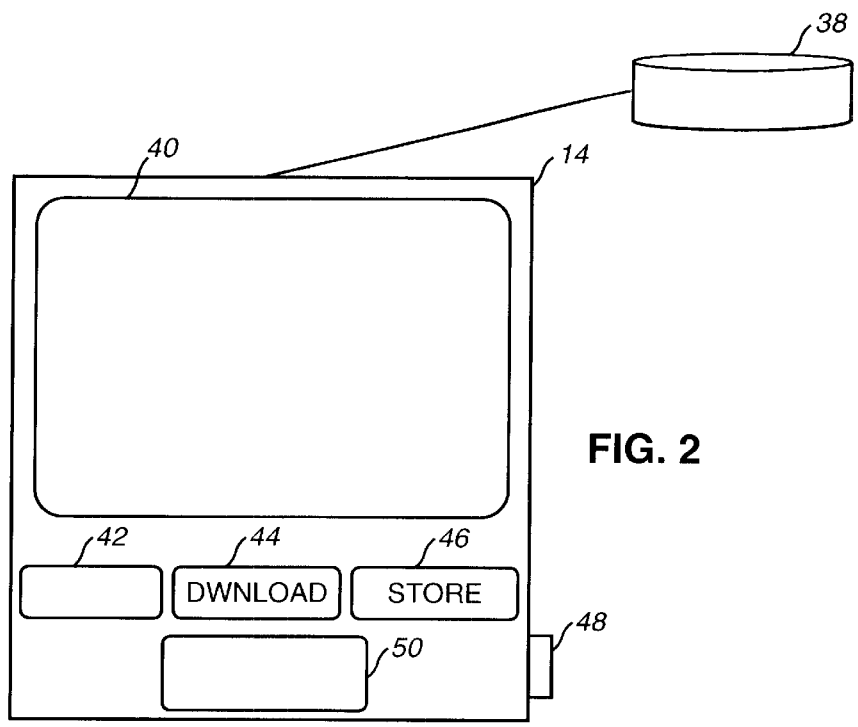
FIG. 2 is a diagram illustrating an example of an external layout of a personal data unit and a monitoring device.

FIG. 2 is a diagram illustrating an example of an external layout of a PDU and a monitoring device in accordance with the present invention. The monitoring device may be any standard medical monitoring device that is capable of providing data to another device. An example shown in FIG. 2 is a wrist or arm band 38 that can monitor pulse, blood pressure, or chemicals secreted by the subject's skin. Another example is a heart monitoring device that can detect heart fibrillation. Another example is a device which fits on a finger for measuring blood oxygenation.

Yet another example is a small chip that may be implanted in the subject's body for taking measurements and/or samples. In such a case, the device would, for example, be able to monitor blood sugar levels for a subject with diabetes. The monitoring device sends data to the PDU, indicating the current status of the condition that is being monitored.

Figure 5:
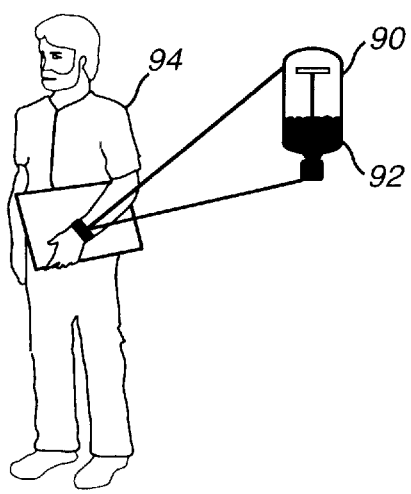
FIG. 5 illustrates an example of a dispense unit worn by a subject.

In addition, the monitoring device may include a dispense unit having a tube which may be implanted in the subject's body and allow for the flow of medicine stored in the tube to the subject's body. FIG. 5 illustrates an example of a dispense unit 90 worn by a subject. The monitoring device may dispense the medication when it receives a signal from the PDU indicating a necessity for medication. The dispense unit together with the monitoring unit may also regulate the subject's chemical levels.

The PDU 14 is a small device designed to be worn by a subject, providing the subject with great mobility. The PDU may include user input/output means. Output means includes a display 40, such as a Liquid/Crystal Display (LCD) screen. The PDU 14 can also be designed with a vibrator and/or a beeper, to notify the subject and other people in the vicinity, of the subject's condition. These output means may be used in combination. For example, if the monitoring device detects a pulse rate above a threshold, the PDU will display a message on the LCD screen, and will also vibrate and/or beep to notify the subject. The message displayed may include the subject's current medical condition as well as brief instructions to the subject to limit their activities.

Input means may include several buttons. For example, a status button 42, when depressed, could cause the PDU to display the current data from the monitoring device; this may include an English translation of any pertinent condition or status detected by the monitoring device.

Another example of an input/output means is a serial communications port 48. A download button 44 may be used in conjunction with the serial communications port 48. The port 48 may be connected to a computer, such as a hospital, clinic or doctor's personal computer, to transfer data stored in the PDU. In this manner, the PDU may be used to store a week's worth of most recent data, for example, while an external computer is used for storing long term data. When the download button 44 is depressed, the PDU transfers data stored in its memory to the external computer. This data can then be reviewed, for example by the subject's doctor, to determine the subject's progress or condition.

A store button 46 may also be used in conjunction with the serial communications port 48 for causing the PDU to receive data from an external source. Such a scheme may be used to reprogram the PDU with various instructions.

A 911 button 50, when depressed could cause the PDU to issue a transmission of an emergency call to a 911 Call Center. This feature enables a user to manually send an emergency page or phone call. This enables the subject to manually seek emergency assistance for a variety of conditions, including injuries from a fall, an automobile malfunction or an imminent danger from criminal activity, and to provide GPS coordinate locations with the emergency call.

Figure 3:
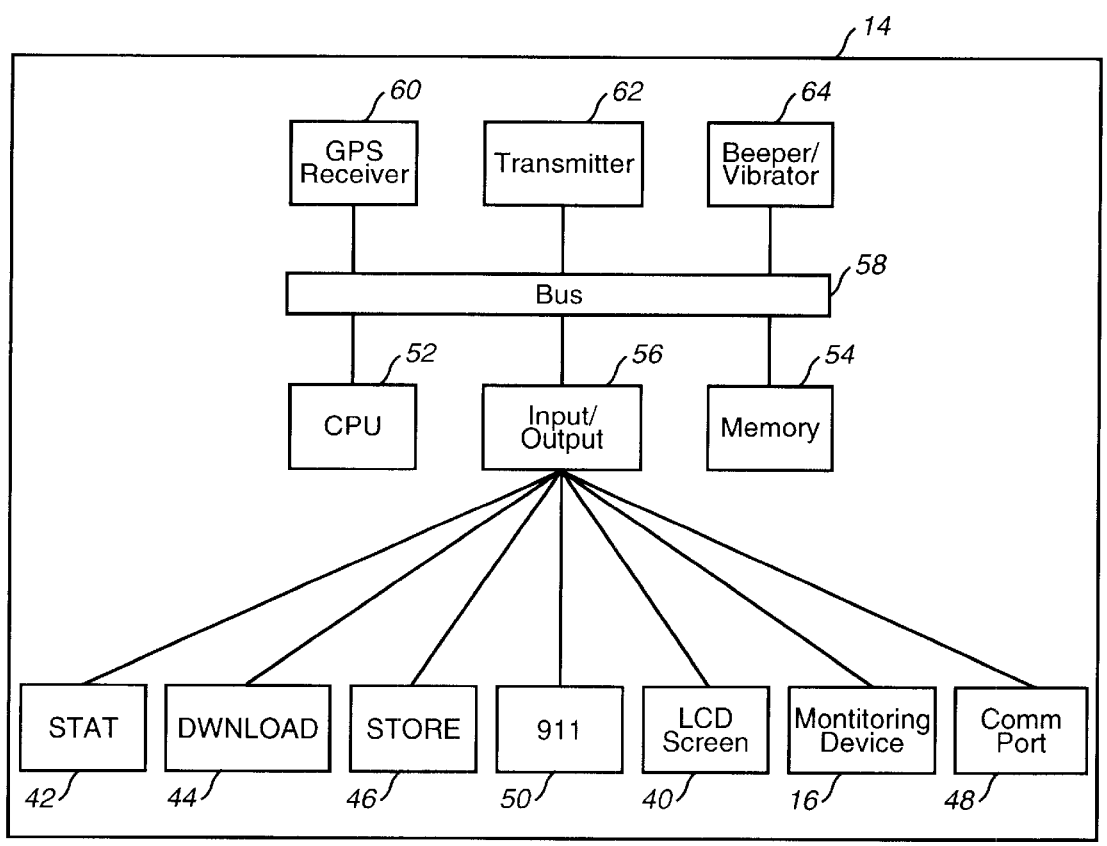
FIG. 3 is a block diagram illustrating an example of a personal data unit's internal components.

FIG. 3 is a block diagram illustrating an exemplary configuration of the PDU's internal components. It comprises a main microprocessor such as a Central Processing Unit (CPU) 52, memory 54, input/output means 56, and a circuit bus 58 for data transfer. As is standard in most computers, memory includes both read only memory (ROM) for permanent data storage and random access memory.

The PDU 14 also includes a transmitter 62. The transmitter 62 is a two-way interactive pager or a digital PCS phone. In a preferred embodiment, an interactive pager is used, because it may be implemented in a smaller device, and the mobility of a subject wearing the PDU is an important factor. The transmission sequence for issuing a page, as well as all alpha-numeric data sent as a page, are stored in PDU's memory 54.

The PDU 14 may also include a GPS receiver 60 which receives signals from GPS satellites, and determines the PDU's current location. The GPS receiver 60 is programmed to write the current coordinates to a place in PDU memory 54 at fixed intervals of time (i.e., once per minute). The PDU memory 54 stores current GPS coordinates, for a predetermined period, and may also store historical coordinates, up to a certain time period.

The PDU 14 may also include input/output means 56 for sequencing input and output calls to the CPU 52 and for formatting data to the appropriate output medium. The input means are buttons for status 42, download 44, store 46, and 911 call 50. The PDU 14 also has a connection for receiving input from the monitoring device 16. All data received from the monitoring device 16 is stored in memory 54. Output means include displays to an LCD screen 40 and downloads via the computer.

The device may also include a beeper and a vibration mechanism 64, as is standard in paging devices. These are binary state components (on/off) and are triggered by instructions that are stored in memory 54 processed by the CPU 52.

A communications port 48 is used to transfer data to and from an external computer, via a direct cable connection. When the download button 44 is depressed, select data values from memory 54 are output to an external computer via the communications port 48; when the store button 46 is depressed, selected data values are input from an external computer and stored in PDU memory 54.

Figure 4:
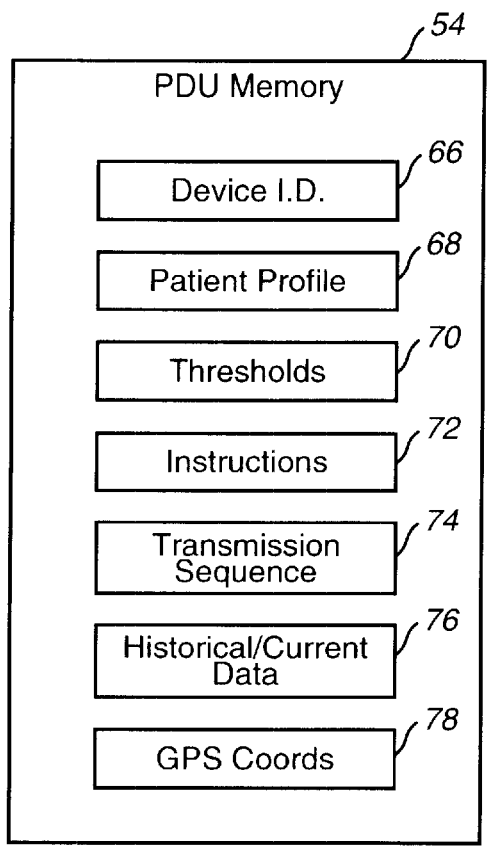
FIG. 4 is a block diagram illustrating an example of a logical data configuration stored in a data storage device.

FIG. 4 is a block diagram illustrating one possible logical configuration of PDU memory. This configuration represents an example of the data stored in memory. Alternate embodiments are possible.

Device ID 66 comprises a unique identifier for each monitoring device. This identifier is included with every transmission performed by the PDU, and is used by the receiving end (e.g., CRS or 911 call center) to identify the source device of each transmission. Each device ID is mapped to a particular subject in the Subject/Device Database, so that the receiving CRS can identify the subject for which a PDU's transmission has been made.

Subject profile 68 includes data for the particular subject wearing the PDU. At a minimum, this may be a subject identifier. The subject identifier may be sent, either in place of or in addition to, the device ID 66, in an emergency transmission. The subject profile 68 may also include other information on the subject, such as name, home address, and medical conditions.

Having a subject profile 68 stored in PDU memory is optional, and is not necessary to enable the present invention. In a first and preferred embodiment, in order to minimize size, a subject profile is not stored in PDU memory. The device ID 66 is included in all transmissions. The CRS uses the device ID as a key to look up the subject profile in the Subject/Device Database.

In a second embodiment, a subject profile 68 is stored in PDU memory 54, but only includes a subject identifier. The subject identifier is included in transmissions, and is used to look up the subject profile in the Subject/Device Database. This embodiment is useful if the PDU (with a single device ID) is to be used by more than one subject. Another button may be added to the PDU for selecting a "current subject", the selection of which causes a certain subject identifier to be used.

In a third embodiment, a complete subject profile is stored in PDU memory 54, including data such as name and medical conditions. This is useful for situations in which a Subject/Device Database is not available. For example, if the PDU transmitter is a PCS phone, and a call is triggered to a 911 call center which does not have access to a CRS or the Subject/Device Database, the PDU may transmit the subject identifier, name, address, medical conditions, current location (from GPS coordinates), and other information as necessary, to the call center.

Thresholds field 70 includes thresholds for data collected from the monitoring device, and used to trigger an action by the PDU. Examples of thresholds include: heart rate or pulse above or below a threshold; body temperature above or below a threshold; blood pressure above or below a threshold; blood sugar level above or below a threshold; or any type of chemical imbalance that may be detected by the monitoring device. Examples of actions that may be triggered are an emergency transmission (page or phone call), activation of the beeper, activation of the vibrator, and an LCD screen display.

Instructions field 72 comprises instructions for the PDU to perform in response to some condition. Instructions are one or more application programs executed by PDU's CPU. Instructions may be grouped, but not limited, into following categories: auto-notification; emergency transmission; data store; and data download.

The auto-notification category includes procedures for triggering output, including displays to the LCD screen, activation of beeper, and activation of vibrator. For example, if pulse rate data collected from the monitoring device exceeds a threshold of 120, auto-notification triggers the activation of the beeper and a display message to the LCD screen.

The emergency transmission category includes procedures for issuing pages or phone calls. These include detection of a threshold, determination of action, retrieval and execution of transmission sequence, and retrieval from memory of data to be included in the transmission (i.e., device ID and subject profile). For example, if data from the monitoring device indicates heart fibrillation, emergency transmission sends a page in accordance with an emergency dialing sequence and transmits device ID, current GPS coordinates, and current data from the monitoring device.

The data store category includes procedures for storing data in PDU memory 54. Data may come from an external computer via the communications port, from the monitoring device, and from the PDU's GPS receiver. The various data are stored in specific allocations of PDU memory.

The data download category includes procedures for downloading data to an external computer via the communications port. The external computer will specify which data to download. PDU instructions specify where to find that data in memory. These instructions may also include security mechanisms, such as user validation of the external computer.

Transmission sequence field 74 includes data needed to issue an emergency transmission. This includes dialing sequences for issuing a page or phone call. A PDU may have more than one transmission sequence. For example, one sequence may be used to call a 911 call center for an emergency condition, and another sequence may be used to call the CRS for nominal status reporting.

Historical/current data field 76 include data collected from the monitoring device for a specified period of time, or for a specified number of data collections. Minimally, current data is stored here, such as the subject's current pulse. This data is extracted and sent in an emergency transmission. Optionally, historical data may also be stored. For example, heart rates collected every 15 minutes for the past week may be stored. This data may be extracted and downloaded to a doctor's computer on a periodic basis.

GPS coordinates field 78 contains current and historical records of GPS coordinates collected by the PDU's GPS receiver.

FIG. 5 illustrates an example of a dispense unit worn by a subject. A tube may be implanted in the subject's body and may allow for the flow of medicine. A dispense unit 90 may be worn by the subject 94 together with the monitoring devices or as a part of the device, and includes medication 92 to be dispensed. The dispensing may be triggered by a signal from the PDU. The PDU may trigger this signal when it determines, from evaluating the medical data collected from the monitoring device, a necessity to dispense medication.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be construed to cohere with all modifications that may fall within the scope of the appended claims.

What is claimed is:

1. A portable medical monitoring device, comprising:
   at least one medical sensor for periodically generating current physiological data relating to a condition of a subject;
   a data storage device for storing said physiological data;
   a transmitter for transmitting said physiological data to a reporting system in response to a first output control signal;
   data processing means for evaluating said physiological data and generating said first output control signal in response to pre-determined parameters in said evaluation, said data processing means generating a plurality of input/output control signals;
   at least one output device communicating at least one of said input/output control signals to said subject; and
   input means for manually initiating download of the physiological data.

2. The portable medical monitoring device as in claim 1, wherein said physiological data is generated in response to said subject's physical condition, including said subject's heart rate, pulse rate, blood pressure, breathing rate, heart EKG activity, or body temperature.

3. The portable medical monitoring device as in claim 1, wherein said first output control signal includes a command to transmit an emergency call.

4. The portable medical monitoring device as in claim 1, wherein said portable medical monitoring device includes a dispense unit having a tube filled with medication, and said first output control signal includes a command to said dispense unit to dispense medication.

5. The portable medical monitoring device as in claim 1, wherein said at least one output device includes a beeper, and one of said plurality of input/output control signals is a signal to activate said beeper.

6. The portable medical monitoring device as in claim 1, wherein said at least one output device includes a vibrator and one of said plurality of input/output control signals is a signal to activate said vibrator.

7. The portable medical monitoring device as in claim 1, wherein said at least one output device includes a screen display, and one of said plurality of output control signals is a signal to display selected data on said screen monitor.

8. The portable medical monitoring device as in claim 1, wherein said transmitter is an interactive paging device whereby a page is sent over a wireless communications network to a central reporting system.

9. The portable medical monitoring device as in claim 1, wherein said transmitter is a PCS network cellular network phone whereby a phone call is made to a central reporting system.

10. The portable medical monitoring device as in claim 1, wherein said data processing means includes a central processing unit (CPU) which interprets and executes instructions.

11. The portable medical monitoring device as in claim 1, wherein said at least one output device includes at least one external data communications port for downloading and uploading said physiological data to an external remote device.

12. The portable medical monitoring device as in claim 11, wherein said external remote device is connected to said central reporting system.

13. The portable medical monitoring device as in claim 1, wherein said physiological data includes a device identification code which identifies a subject to said central reporting system.

14. The portable medical monitoring device as in claim 13, wherein said physiological data transmitted by said transmitter further comprises a subject profile including subject's name, home address, and medical conditions.

15. A portable medical monitoring device, comprising:
 at least one medical sensor for periodically generating current physiological data relating to a condition of a subject;
 a data storage device for storing said physiological data;
 a Global Positioning System (GPS) receiver for determining geographic coordinates of the subject;
 a wireless transmitter for transmitting said physiological data and said geographic coordinates to a reporting system in response to a first output control signal;
 data processing means for evaluating said physiological data and generating said first output control signal and a plurality of other output control signals;
 at least one output device for communicating with said subject in response to at least one of said other output control signals; and
 input means for manually initiating one of downloading of the physiological data and transmission of the geographic coordinates.

16. The portable medical monitoring device as in claim 15, wherein said physiological data is generated in response to said subject's physical condition, including said subject's heart rate, pulse rate, blood pressure, breathing rate, heart EKG activity, or body temperature.

17. The portable medical monitoring device as in claim 15, wherein one of said plurality of other output control signals is an instruction to transmit an emergency call which includes said geographic coordinates.

18. The portable medical monitoring device as in claim 15, wherein said at least one output device includes a beeper, and one of said plurality of other output control signals is a signal to activate said beeper.

19. The portable medical monitoring device as in claim 15, wherein said at least one output device includes a screen display, and one of said plurality of other output control signals is a signal to display selected data on said screen monitor.

20. The portable medical monitoring device as in claim 15, wherein said transmitter is an interactive paging device whereby a page is sent over a wireless communications network to a central reporting system, said page including the subject's geographic coordinates.

21. The portable medical monitoring device as in claim 15, wherein said transmitter is a PCS network cellular network phone whereby a phone call is made to a central reporting system to transmit data thereto, said data including said geographic coordinates.

22. The portable medical monitoring device as in claim 21, wherein said central reporting system may dispatch emergency services to the geographic coordinates in response to an emergency call from said device.

23. The portable medical monitoring device as in claim 15, wherein said data processing means includes a central processing unit (CPU) which interprets and executes instructions relating to said medical data.

24. The portable medical monitoring device as in claim 15, wherein said at least one output device includes at least one external data communications port for downloading and uploading said physiological data to an external data store at said central reporting system.

25. The portable medical monitoring device as is claim 15, wherein said physiological data includes a device identification code which identifies a subject to said central reporting system.

26. The portable medical monitoring device as in claim 25, wherein said physiological data transmitted by said transmitter further comprises a subject profile including subject's name, home address, and medical conditions.

27. A medical monitoring system for collection and evaluation of a subject's physiological data comprising:
 a plurality of portable medical monitoring devices, each of the plurality of said portable medical monitoring devices comprising,
  at least one medical sensor for to periodically generating current physiological data relating to a condition of said subject;
  a data storage device for storing said physiological data from said at least one medical sensor;
  a wireless transmitter for transmitting said physiological data to a reporting system in response to a first output control signal;
  data processing means for evaluating said physiological data and generating a plurality of output control signals;
  at least one output device for communicating information in response to at least one of a plurality of input/output control signals; and
  an input means for manually initiating download of the physiological data; and
 a reporting data server for collecting and storing physiological data from the plurality of said portable medical monitoring devices wherein each of said portable medical monitoring devices has a unique device identifier and monitors a separate subject, said reporting data server further comprising means for correlating said unique device identifier to an individual subject medical data record.

28. The medical monitoring system as claimed in claim 27, wherein said central reporting service further comprises means to respond to emergency calls from said medical monitoring devices.

29. The medical monitoring system as in claim 28, wherein said means for responding to emergency calls from said medical monitoring device comprises a processor capable of executing instructions and automatically referencing said device identifier to physiological data relating to a particular subject and issuing a second call to a selected authority and transmitting said physiological data with said second call to said authority.

30. The medical monitoring system as in claim 28, wherein said portable medical monitoring device further includes a GPS receiver and said central reporting system records geographic coordinates of the subject for each emergency call.

31. The medical monitoring system as in claim 27, wherein said medical monitoring system further includes a database where said physiological data and related information pertaining to each subject are stored and retrieved by said central reporting system at predefined intervals.

32. A portable medical monitoring device comprising:
a medical sensor adapted to be coupled to a subject;
a memory configured to store physiological data received from a medical sensor;
processor configured to evaluate the physiological data and to generate a control signal based on the evaluation;
a transmitter for transmitting the physiological data of the subject to a reporting system in response to the control signal; and
input means for manually initiating download of the physiological data.

33. The portable medical monitoring device as in claim 32, wherein the processor automatically generates the control signal to initiate an emergency call.

34. The portable medical monitoring device as in claim 32, wherein the processor is further configured to generate another control signal to an output device to notify the subject.

35. The portable medical monitoring device as in claim 32, wherein the sensor is adapted for internal use within the subject.

36. The portable medical monitoring device as in claim 32, further comprising:
a dispense unit configured to dispense fluid into the subject in response to the control signal.

* * * * *